United States Patent [19]

Hirai et al.

[11] 3,939,167

[45] Feb. 17, 1976

[54] 3-(2-METHYLTHIO-2-TERTIARY AMINOACETYL)-5-PHENYLISOXAZOLES

[75] Inventors: Shoichi Hirai, Ibaraki; Kyozo Kawata, Kawanishi, both of Japan

[73] Assignee: Shionogi & Co., Ltd., Osaka, Japan

[22] Filed: Aug. 21, 1973

[21] Appl. No.: 389,636

[30] Foreign Application Priority Data

Aug. 22, 1972 Japan.................................. 47-83916

[52] U.S. Cl. ................. 260/293.67; 260/243 B; 260/247.1 M; 260/268 C; 260/307 H; 424/246; 424/248; 424/250; 424/267; 424/272

[51] Int. Cl.²........................................ C07D 295/12

[58] Field of Search.................... 260/293.67, 307 H

[56] References Cited
UNITED STATES PATENTS

| | | | |
|---|---|---|---|
| 3,321,474 | 5/1967 | Kano et al. | 260/293.67 |
| 3,321,475 | 5/1967 | Kano et al. | 260/307 H |
| 3,752,819 | 8/1973 | Philippe | 260/307 H |

*Primary Examiner*—Sherman D. Winters
*Attorney, Agent, or Firm*—Stewart and Kolasch, Ltd.

[57] ABSTRACT

A phenylisoxazole of the formula:

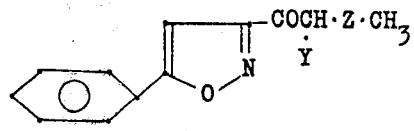

wherein, Y represents a hydrogen atom, a halogen atom, an alkali metal atom or a tertiary amino group and Z represents a sulfur atom or a sulfoxide group. They are prepared by subjecting 3-alkoxycarbonyl-5-phenylisoxazole to a treatment with at least one agent selected from the group consisting where required and as necessary of dimethyl sulfoxide, a neutralizing agent, an agent capable of releasing a halogen ion and a secondary amine at a temperature ranging from about −5°C to about 70°C for a time period from several minutes up to about 4 hours.

The phenylisoxazoles are useful as intermediates for preparing a 3-(2-tertiary amino-1-hydroxyethyl)-5-phenylisoxazole, any of which is known as useful medicaments having a remarkable analgesic, antispasmodic, antiphretic, antiallergic, antiinflammatory, antitussive activity or the like, each reflecting the species of the substituent tertiary amino groups and generally having a very low toxicity.

8 Claims, No Drawings

3-(2-METHYLTHIO-2-TERTIARY AMINOACETYL)-5-PHENYLISOXAZOLES

BACKGROUND OF THE INVENTION

1. Field of the Invention

The present invention generally relates to phenylisoxazole derivatives. More specifically, it is concerned with 5-phenylisoxazole derivatives which are useful as intermediates for the production of 3-(2-tertiary amino-1-hydroxyethyl)-5-phenylisoxazoles known as useful medicaments having a remarkable analgesic activity, antispasmodic activity, antipyretic activity, antiallergic activity, antiinflammatory activity, antitussive activity or the like, each reflecting the species of the substituent tertiary amino group and generally having a very low toxicity. The present invention also relates to processes for preparing such 5-phenylisoxazole derivatives as well as a process composed of consecutive stages yielding as its final product, 3-(2-tertiary amino-1-hydroxyethyl)-5-phenylisoxazoles, which process includes a preparing method for precursors each of which sequentially leads to these final products.

2. Description of the Prior Art

It has hitherto been believed that a Grignard reaction is indispensable for the preparation of the compounds of this kind. Although the actual production of these compounds is performed by employing the Grignard reaction, this has been hindered because of the expensive material cost and the reaction period required for the overall process. Therefore, an advent of any scheme which can eliminate the Grignard reaction has long been awaited because it would facilitate the production and eventually curtail the manufacturing cost drastically.

Summary of the Invention

It is therefore the primary object of the present invention to provide novel phenylisoxazole derivatives, each of which sequentially leads to the final product, a 3-(2-tertiary amino-1-hydroxyethyl)-5-phenylisoxazole.

It is another object of the present invention to provide a novel process composed of consecutive stages yielding, as its final product, a 3-(2-tertiary amino-1-hydroxyethyl)-phenylisoxazole.

It is a further object of the present invention to provide novel processes for preparing each of said novel phenylisoxazole derivatives.

It is still another object of the present invention to provide the best possible measure for eliminating the Grignard reaction which has been believed to be indispensable for the production of the compounds of this kind but which has been imposing many problems not feasibly solved on the production of the final product.

According to the present invention, there is provided a phenylisoxazole of the formula:

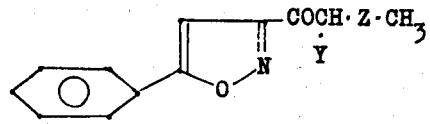

wherein, Y represents a hydrogen atom, a halogen atom, an alkali metal atom or a tertiary amino group and Z represents a sulfur atom or a sulfoxide group, and a method for preparing said phenylisoxazole which comprises; subjecting 3-alkoxycarbonyl-5-phenylisoxazole to a treatment with at least one agent selected from the group consisting where required and as necessary of dimethyl sulfoxide, a neutralizing agent, an agent capable of releasing a halogen ion and a secondary amine.

More detailedly, the method of the present invention comprises a reaction of the starting material, 3-alkoxycarbonyl-5-phenylisoxazole [I] with dimethylsulfoxide in the presence of a base to yield 3-methylsulfinyl-(alkali metal)acetyl-5-phenylisoxazole [II] which is subsequently halogenated to 3-(2-methylthio-2-halogenoacetyl)-5-phenylisoxazole [III], and a reaction of the compound [III] with a secondary amine to give 3-(2-methylthio-2-tertiary aminoacetyl)-5-phenylisoxazole [IV] which is subsequently reduced to 3-(2-tertiary amino-1-hydroxyethyl)-5-phenylisoxazole [V] with a hydrogenated metal complex compound. Prior to the halogenation, the compound [II] may optionally be neutralized with an acid to yield 3-methylsulfinylacetyl-5-phenylisoxazole [II']. The process can be illustrated in the following schemes.

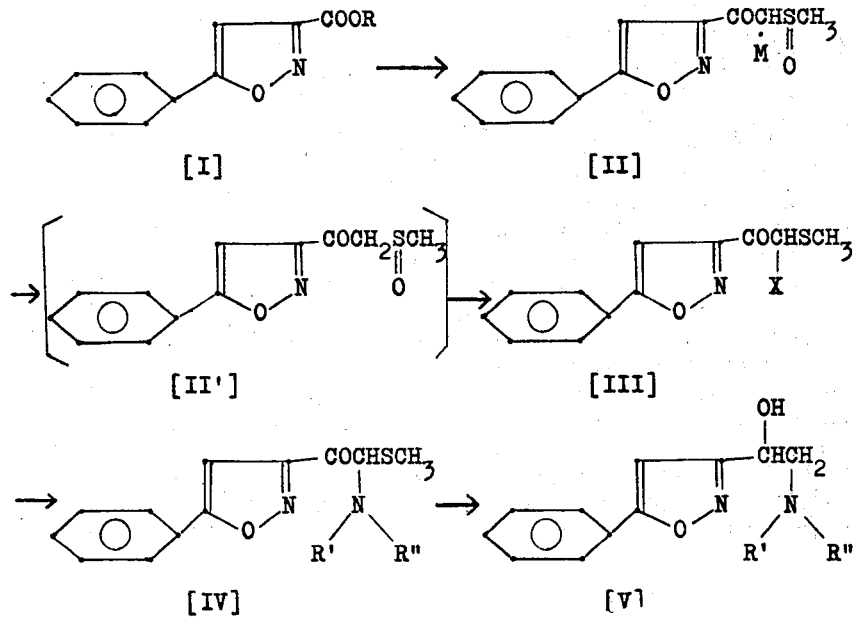

[wherein, R, R' and R'' each represents a lower alkyl group, the

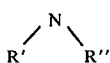

group may be a cyclic amino group wherein R' and R'' are combined together directly or through a hetero atom to form a closed ring, M represents an alkali metal atom, and X represents a halogen atom ].

The starting material of the process of the present invention, 3-alkoxycarbonyl-5-phenylisoxazole [I] can be obtainable through ring closure of a corresponding pyruvate ester with hydroxylamine. The lower alkyl group indicated by R in the compound [I] is, in general, a methyl or ethyl group, though it may be another group and the difference in the number of the carbon atoms included in the alkyl group is not significant.

The first step of the present invention is the reaction of the compound [I] with dimethylsulfoxide under a basic condition, i.e., in the presence of sodium hydride, sodium amides, alkoxides of alkali metals, for instance, sodium methoxide, potassium tert-butoxide and the like, and may be performed without any solvent, i.e. through utilization of dimethylsulfoxide itself as a solvent or with an inert solvent such as benzene, toluene, tetrahydrafran, dioxane, diethyl ether or the like at a temperature ranging from about −5°C to about 40°C. A time period ranging from several minutes to about 2 hours is sufficient to obtain the compound [II] in a good yield. The compound [II] may tautomerically take an enol form of the formula:

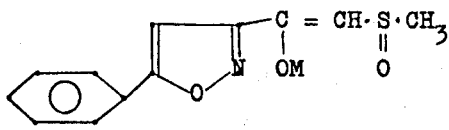

beside the illustrated keto form and may be used as the starting material of the next step as it is, though it may, if required, further be neutralized to the compound [II'] in a known conventional manner. The neutralization can be performed with any acid to yield the free compound [II'] immediately.

The next, the second, step of the process is a halogenation of the compound [II] or [II'] with an agent capable of releasing a halogen ion, for example, hydrogen halides, acetyl halides or thionyl halides, and may be performed in a solvent such as dichloromethane, chloroform or esters of acetic acid at a room temperature (about −5°∼+30°C) to obtain the compound [III]. A short time period (shorter than about 1 hour) is required for the reaction. When the hydrogen halide is used, utilization of a solvent, especially, ethyl acetate saturated with gaseous hydrogen halide is particularly convenient.

The obtained halide [III] is however substantially unstable and easily decomposed in the presence of water or an alcohol to such an extent that its precise identification is considerably difficult, and therefore is presumed to have a structure indicated by formula [III] in view of the precursor [II] and the product [IV] of the subsequent step of the process.

The third step is a process wherein, the halide [III] thus obtained is combined with a secondary amine which includes dimethylamine, diethylamine, dipropylamine, methylethylamine or methylisopropylamine, or a heterocyclic amine of pyrrolidine, piperidine, N-acetylpiperazine, morpholine or thiomorpholine. This step may normally be performed by dropwise addition of said secondary amine into a solution or a suspension of the halide [III] in an inert solvent which includes benzene, toluene, dichloromethane, tetrahydrofuran, dioxane or diethyl ether, at a temperature ranging from about −5°C to about 50°C.

Said secondary amine may optionally be dissolved or suspended in an inert solvent of the described class prior to the addition which may be effected while being stirred and then this stirring is continued for a time period of about 0.5 hour up to about 4 hours to give the compound [VI] having the corresponding tertiary amino group.

The final step is the process of reducing the compound [IV] with a hydrogenated metal complex compound, for instance, alkali metal borohydrides ($NaBH_4$, $LiBH_4$ and $KBH_4$), alkali metal aluminum hydrides ($NaAlH_4$ and $LiAlH_4$), sodium borohydride cyanide ($NaBH_3CN$), aluminum sodium bis (2-methoxyethoxy)hydride ($NaAl(OC_2H_5OCH_3)_2H_2$) or aluminum sodium diethyl dihydride ($NaAl(C_2H_5)_2H_2$), and the reaction proceeds successfully by adding said hydrogenated metal complex compound to the compound [IV] dissolved or suspended in a solvent of preferably alcohols at a temperature ranging from 0°C to about 70°C. A time period of several minutes up to about 2 hours is sufficient for giving the compound [V] in a high yield.

It is to be noted that when a compound with a weakly basic secondary amine such as morpholine is used in the reduction step as the compound [IV], more vigorous reaction conditions will be required to effect smooth elimination of the methylthio group. Moreover, the yield of the obtained compound [V] is still considerably low even when such vigorous conditions are employed.

In actual operation, the whole of the above described steps may be performed continuously in a single batch, i.e., each product of the consecutive steps may be passed into the subsequent step as its starting material without being isolated from the reaction mixture or being subjected to any purifying treatments.

The 3-tertiary aminoethyl-5-phenylisoxazole derivatives thus obtained, are excellent medicaments as have been described in the beginning of the specification. They may however include oily substances which themselves are not suitable for administration in some instances and their basic nature may sometimes be not advantageous for medicaments from the preparative point of view. For such reason, they may be converted into any pharmaceutically acceptable salts, i.e., acid addition salts, with or without any previous isolation or purification.

Selection of the intended salts depends on the object as to whether it is performed for the facility in purification or for the feasibility in preparation. Normally, such salts include inorganic salts such as the hydrochloride, sulfate, nitrate, hydrobromide, hydroiodide, phosphate, thiocyanide, carbonate and perchlorate, and organic salts such as the propionate, oxalate, tartrate, citrate, succinate, salicylate, benzoate, picrate and palmitate.

These salts can be obtainable by placing the above aminoalkylphenylisoxazoles in a reaction with the corresponding acids or in an anion exchanging reaction, and its actual operation proceeds in accordance with any conventional method of preparing organic salts.

As has been briefly described, the processes of the present invention and the key intermediary products of the process, are of great commercial importance because they are very excellent novel means for preparing 3-(2-tertiary amino-1-hydroxyethyl)-5-phenylisoxazoles, being useful as precursors successively leading to said final product.

Especially, the intermediate product of the second step, 3-methylsulfinyl(alkali metal)acetyl-5-phenylisoxazole (alkali metal 1-(5-phenylisoxazole-3-yl)-2-methylsulfinylethenoxide) or 3-methylsulfinylacetyl-5-phenylisoxazole, may be derived into 3-acetyl-5-phenylisoxazole directly or through an intermediate, 3-(2-methylsulfinyl-1-hydroxyethyl)-5-phenylisoxazole. This will provide another possibility of reaching the final product, i.e., alternate paths leading to the final product.

DESCRIPTION OF THE PREFERRED EMBODIMENTS

In the following description, the processes of the present invention will be described in more detail by way of examples.

EXAMPLE 1 (the first step, 1)

Oily (50%) sodium hydride (1.2 g, 0.025 mole) and dimethylsulfoxide (12 ml) are intimately mixed under nitrogen atmosphere and the mixture is heated to 70°C while being stirred. After the evolution of hydrogen gas from the reaction mixture has ceased (in about 20 min.), it is cooled to room temperature and then thereto is added 4 ml of tetrahydrofran.

To the mixture, there is added 2 g (0.01 mole) of 3-methoxycarbonyl-5-phenylisoxazole dissolved in 8 ml of tetrahydrofran dropwise in about 7 minutes while being ice-cooled and stirred.

The mixture is then allowed to react with stirring at room temperature for about 30 minutes until it becomes highly viscous, and is poured into 75 ml of ice water and neutralized with 6 ml of 6N hydrochloric acid until it becomes weakly acidic (pH ≈ 3) to precipitate white crystals.

The obtained mixture is extracted four times with 100 ml of chloroform each time and the respective chloroform layers are combined together and washed three times with 50 ml of water each time.

The washed chloroform layer is dried over sodium sulfate and the solvent is expelled by evaporation under reduced pressure leaving 2.92 g of white crystals which are then washed with diethylether and recrystallized from ethyl acetate to give needles of 3-methylsulphinylacetyl-5-phenylisoxazole (2.00 g, 80.5%). mp. 164°–166°C.

Anal. Calcd. for: $C_{12}H_{11}O_3NS$ (Mw: 249.2). C,57.83; H,4.45; N,5.62; S,12.84. Found: C,57.37; H,4.47; N,5.74; S,12.57.

IR: $\nu_{Max}^{CHCl_3}$(cm$^{-1}$) 1700, 1615, 1575, 1498, 1433, 1060, 1040, 945.

EXAMPLE 2 (the first step, 2)

Sodium amide (90 %, 43.5 g, 1.0 mole) and dimethylsulfoxide (300 ml) are intimately mixed under a nitrogen atmosphere and the mixture is stirred at 70°–75°C for about 30 minutes until the evolution of gaseous ammonia ceases, which mixture is subsequently ice-cooled for about 30 minutes.

To this ice-cooled reaction mixture there is added 101.5 g (0.5 mole) of 3-methoxycarbonyl-5-phenylisoxazole dissolved in 300 ml of tetrahydrofran dropwise in about 30 minutes.

After the dropwise addition, the reaction mixture is stirred at room temperature for about one hour during which period it begins to solidify within about 10 minutes after the initiation of the stirring.

Ice water of about 2.5 is poured into this mixture to dissolve the precipitates. The mixture is then neutralized with about 220 ml of 6N hydrochloric acid until its pH value reaches about 2 to precipitate white crystals.

The crystals are dissolved in 1.5 of chloroform and the chloroform solution is washed with 500 ml of water and dried over sodium sulfate. The solvent in the solution is removed by evaporation under reduced pressure to give 105.6 g of crystalline residue.

Recrystallization of the residue from diethylether affords needles of 3-methylsulfinylacetylisoxazole (98.2 g, 78.7 %). mp 164°–166°C.

EXAMPLE 3 (The second step, 1)

To a suspension of 1.25 g (5.016 milimoles) of 3-methylsulfinylisoxazole in 20 ml of dichloromethane, there is added 1.6 g (10.05 milimoles) of a solution (23 %) of hydrogen chloride in ethyl acetate at room temperature, and the mixture is stirred at the same temperature for about 25 minutes.

This pale red solution is concentrated to dryness under reduced pressure at a bath temperature of 28.5°C to thoroughly expel the solvent out and to obtain crude 3-(2-methylthio-2-chloroacetyl)-5-phenylisoxazole (1.3258 g, 99.3 %) as a crystalline residue.

IR: $\nu_{Max}^{CHCl_3}$ (cm$^{-1}$) 1712, 1610, 1570, 1495, 1442, 1430, 1045, 945.

EXAMPLE 4 (the third step, 1)

The crude crystals of 3-(2-methylthio-2-chloroacetyl)-5-phenylisoxazole (1.32 g, 5.0 milimoles) obtained in the above Example 3 are suspended in 20 ml of benzene without being further purified, and the suspension is combined with 984 mg (11.5 milimoles) of piperidine while being stirred and ice-cooled.

After the combination, the mixture is lifted from the ice and stirred at room temperature for about 2 hours. The precipitant in the reaction mixture is removed by filtration with a No. 3 glass filter and the obtained filtrate (50 ml as a whole) is combined with 30 ml of water to be washed once. After being dried over sodium sulfate, the benzene in the filtrate is removed by evaporation under reduced pressure to give 1.63 g of crystalline residue. Recrystallization of this residue from methanol affords needles of 3-(2-methylthio-2-piperidinoacetyl)-5-phenylisoxazole (0.861 g, 54.3 %, calculated based on the starting material of the preceding step). mp. 113°–115°C.

Anal. Calcd. for: $C_{17}H_{20}O_2N_2S$ (Mw: 316.35). C, 64.54; H, 6.37; N, 8.86; S, 10.13. Found: C, 64.32; H, 6.14; N, 8.90; S, 10.11.

IR: $\nu_{Max}^{CHCl_3}$ (cm$^{-1}$) 2940, 1705, 1615, 1575, 1495, 1445, 1175, 1118, 1100, 950, 918, 1055.

EXAMPLE 5 (the fourth (final) step, 1)

The crude crystals of 3-(2-methylthio-2-piperidinoacetyl)-5-phenylisoxazole (1.631 g) obtained in Example 4 above, are suspended in 20 ml of methanol without being further purified and the suspension is stirred after a portionwise addition (in about 10 minutes) of 143 mg (3.78 millimoles) of sodium borohydride at room temperature for about 30 minutes.

The methanol in the reaction mixture (pale yellow solution) is then removed by evaporation under reduced pressure to leave a residue which is subsequently dissolved in 30 ml of benzene. The benzene solution is shaken four times with 20 ml of 4N hydrochloric acid each time to extract the basic substance. Each of the hydrochloric acid layers is washed once with 20 ml of benzene and combined together to be neutralized with potassium carbonate while being ice-cooled until it becomes basic (pH ≈ 10). The liberated crystalline substance is extracted twice with 50 ml of dichloromethane each time. After being separated, the dichloromethane layers are combined and washed once with 30 ml of water and dried over sodium sulfate, and the solvent of the layer is removed by evaporation under reduced pressure to leave a crystalline residue (72.56 mg, 53%, crude yield, calculated based on the starting material of Example 3 (the second step)).

Recrystallization of this product from dichloromethane-ether (1:4) affords needles of 3-(2-piperidino-1-hydroxyethyl)-5-phenylisoxazole (701 mg, 51.3% as an overall yield calculated based on the starting material of Example 3 (the second step)). mp. 104°–106°C.

Identification of this product with an authentic sample was carried out by mixed melting and by comparing their infrared absorption spectra.

EXAMPLE 6 (the second step, 2)

A reaction identical with that of Example 3 is performed on the 3-methylsulfinylacetyl-5-phenylisoxazole (1.25 g) prepared in a manner similar to that described in Example 1 or 2 with the exception that the ethyl acetate solution of hydrogen chloride is replaced by a solution of acetyl bromide (741 mg, 6.025 milimoles) in dichloromethane (10 ml) to give 3-(2-methylthio-2-bromoacetyl)-5-phenylisoxazole (1.62 g, 103.5 %) as a crude crystalline residue.

IR: $\nu_{Max}^{CHCl_3}$ (cm$^{-1}$) 1710, 1610, 1588, 1568, 1440, 1425, 1042, 945.

EXAMPLE 7 (the third step, 2)

The crude crystals (residue) of 3-(2-methylthio-2bromoacetyl)-5-phenylisoxazole (1.62 g, 5.03 millimoles) obtained in Example 6 above, are dissolved in 10 ml of benzene without being further purified. To this solution, there is added portionwise a solution of 990 mg (11.6 millimoles) of piperidine in 10 ml of benzene in about 2 minutes while being ice-cooled and stirred. After the portionwise addition, the mixture is brought to the environment at room temperature and further stirred for about 80 minutes.

A filtrate obtained by removing the precipitant from the reaction mixture is shaken four times with 20 ml of 4N hydrochloric acid each time in a conventional manner to thoroughly extract the basic substance, and each of the hydrochloric acid layers is washed once with 20 ml of benzene.

The washed hydrochloric acid layers are combined together and neutralized with potassium carbonate until it becomes basic (pH ≈ 10) to liberate crystals which are then extracted twice with 50 ml of dichloromethane each time.

After being washed with 30 ml of water, the combined dichloromethane layer is dried over sodium sulfate and the solvent is removed by evaporation under reduced pressure from the layer to give a crystalline residue (1.253 g, 79 %). Recrystallization of the crude crystals from methanol affords needles of 3-(2-methylthio-2-piperidinoacetyl)-5-phenylisoxazole (1.1249 g, 70.8 % calculated based on the starting material of the precedent step). mp. 113°–115°C.

This was identified with an authentic sample by mixed melting and in terms of the infrared absorption spectra.

EXAMPLE 8 (the third step, 3)

The crystalline residue of 3-(2-methylthio-2-bromoacetyl)-5-phenylisoxazole (1.63 g) obtained by a manner similar to that described in Example 6 is combined with 10 ml of benzene. To this mixture is added portionwise (in about 1 minute) a solution (43 %) of dimethylamine (1.1 g, equivalent to 523 mg) in benzene diluted further with another 10 ml of benzene while being ice-cooled and stirred.

After the addition, the reaction mixture is lifted from the ice bath and further stirred at room temperature for about 1.5 hours.

Treatment of the mixture similarly to that described in the latter half of Example 7 gives a crystalline residue (1.11 g). Recrystallization of this residue from dichloromethane-ether (1:4) affords needles of 3-(2-methylthio-2-dimethylaminoacetyl)-5-phenylisoxazole (1.005 g, 72.5 % calculated based on the starting material of the precedent step). mp. 98°–99.5°C.

Anal. Calcd. for: $C_{14}H_{16}O_2N_2S$ (Mw: 276.28) C, 60.86; H, 5.84; N, 10.14; S, 11.58. Found: C, 60.18; H, 5.87; N, 9.70; S, 10.87.

IR: $\nu_{Max}^{CHCl_3}$ (cm$^{-1}$) 2830, 2780, 1700, 1610, 1570, 1440, 1170, 1035, 945.

EXAMPLE 9 (the fourth (final) step, 3)

To a suspension of 3-(2-methylthio-2-dimethylaminoacetyl)-5-phenylisoxazole (461 mg, 1.67 millimoles) obtained in Example 8 in 5 ml of methanol, there is added 47.4 mg (1.25 millimoles) of sodium borohydride in about 3 minutes while being stirred at room temperature and the stirring is still continued for about 30 minutes.

A crystalline residue obtained by concentration under reduced pressure of the reaction mixture is dissolved in 30 ml of benzene and shaken with 30 ml of water to effect solubilization of the remaining residue and extraction. The extract is treated in a manner similar to that described in Example 5 to give a crystalline residue of 370.2 mg which is subsequently recrystallized from dichloromethane-ether (1:4) to afford needles of 3-(2-dimethylamino-1-hydroxyethyl)-5-phenylisoxazole (340.4 mg, 90.1 %). mp. 117°–119°C.

Anal. Calcd. for: $C_{13}H_{16}O_2N_2$ (Mw: 232.2) C, 67.22; H, 6.94; N, 12.06. Found: C, 67.41; H, 7.04; N, 11.80.

IR: $\nu_{Max}^{CHCl_3}$ (cm$^{-1}$) 3400(broad), 2830, 2780, 1610, 1575, 1440, 1085, 1020, 945, 885, 855.

EXAMPLE 10 (the third step, 4)

The crude crystals of 3-(2-methylthio-2-chloroacetyl)-5-phenylisoxazole (1.369 g) obtained in a manner similar to that as described in Example 3 wherein the ethyl acetate solution of hydrogen chloride is replaced by 473 mg (0.43 ml) of acetyl chloride, are dissolved in 10 ml of benzene.

To this mixture still containing some insoluble substance, there is added dropwise a solution of piperidine (990 mg) in benzene (10 ml) in about 3 minutes while being stirred and ice-cooled. After the dropwise addition, the mixture is lifted from the ice bath to be stirred at room temperature for about 2 hours.

The reaction mixture (suspension) is aspirated with a No. 3 glass filter and washed with 15 ml of benzene to remove the piperidine hydrochloride. The benzene layer is shaken four times with 20 ml of 4N hydrochloric acid each time. The hydrochloric acid layers are combined together and neutralized to make the mixture basic (pH ≈ 10) and to liberate crystals which are subsequently extracted twice with 50 ml of benzene each time.

The benzene layers are combined, washed twice with 30 ml of water each time and dried over sodium sulfate. The solvent in the layer is removed by evaporation under reduced pressure to give a crystalline residue (938.1 mg, 59 % calculated based on the starting material of the precedent step).

Recrystallization of the crude crystals from dichloromethane-ether (1:4) affords needles of 3-(2-methylthio-2piperidinoacetyl)-5-phenylisoxazole (839.2 mg, 52.7 % calculated based on the starting material of the precedent step). mp. 111°–115°C.

This product was identified with an authentic sample by mixed melting and by comparing their infrared absorption spectra.

EXAMPLE 11 (the third step, 5)

The crude crystals of 3-(2-methylthio-2-chloroacetyl)-5-phenylisoxazole (1.457 g) obtained in a manner similar to that as described in Example 3, are allowed to react with dimethylamine (benzene solution (48%) 1.09 g, equivalent to 520 mg) in a manner similar to Example 8 to give a crystalline residue (931 mg).

Recrystallization of this product from dichloromethane-ether (1:4) affords needles of 3-(2-methylthio-2dimethylaminoacetyl)-5-phenylisoxazole (845 mg, 61 % calculated based on the starting material of the precedent step). mp. 98°–99.5°C.

Identification of this product with the authentic sample (Example 10) was carried out by mixed melting and by comparing their infrared absorption spectra.

EXAMPLE 12 (the third step, 6)

The crude crystals of 3-(2-methylthio-2-bromoacetyl)-5-phenylisoxazole (1.573 g) obtained by a manner similar to that as described in Example 6, are suspended in 10 ml of benzene. To this suspension, there is added dropwise a solution of morpholine (1.007 g) in benzene (10 ml) while being stirred and ice-cooled. After the dropwise addition, the mixture is lifted from the ice bath to be stirred at room temperature for about 1 hour.

The reaction mixture (suspension) is aspirated with a No. 3 glass filter and washed with 30 ml of benzene to remove the resultant morpholine hydrobromide salt (642.5 mg). The benzene layer of the filtrate is washed twice with 50 ml of water each time and the water layers are extracted with 50 ml of benzene. The combined benzene layer is then dried over sodium sulfate and the solvent in the mixture is removed by evaporation under reduced pressure to give a crystalline residue (1.504 g).

The crude crystals are fractionated by chromatography with a column of silica gel (Wakogel C-200 (trade name), 25 g) to obtain a crystalline substance (1.261 g) from both fractions with the eluants petroleum ether-benzene (1:2) and benzene-chloroform (1:1).

Recrystallization of this product from methanol affords pillars of 3-(2-methylthio-2-morpholinoacetyl)-5phenylisoxazole (1.177 g, 73.7 %). mp. 124°–126°C.

Anal. Calcd. for: $C_{16}H_{18}O_3N_2S$. C, 60.37; H, 5.70; N, 8.80; S, 10.05. Found: C, 60.12; H, 5.65; N, 8.62; S, 9.89.

IR: $\nu_{Max}^{CHCl_3}$ (cm$^{-1}$) 2965, 2875, 1705, 1615, 1575, 1495, 1445, 1260, 1140, 1115, 1055, 1010, 950, 925.

EXAMPLE 13 (the third step, 7)

The crude crystals of 3-(2-methylthio-2-chloroacetyl)-5-phenylisoxazole (1.38 g) obtained in a manner similar to that as described in Example 3 are treated in the same manner as Example 12 to give 3-(2-methylthio-2-morpholinoacetyl)-5-phenylisoxazole (1.071 g, 67.0 % calculated based on the starting material of the precedent step).

EXAMPLE 14 (the fourth (final) step, 4)

3-(2-Methylthio-2-morpholinoacetyl)-5-phenylisoxazole (700 mg, 2.2 millimoles) obtained in a manner similar to that as described in either of Example 12 or 13, is suspended in 16 ml of methanol. To this suspension, there is added portionwise sodium borohydride (152.7 mg, 4.04 millimoles) at 50°C in about 10 minutes. After the addition, the suspension is stirred at 60°C for about 30 minutes.

The solvent in the reaction mixture is removed by evaporation under reduced pressure to leave a residue which is subsequently extracted twice with 30 ml of benzene each time after addition of 30 ml of water. The extract is washed twice with 30 ml of water each time and dried over sodium sulfate. Removal of the solvent by evaporation under reduced pressure from the mixture gives a crystalline residue (0.25 g).

Recrystallization of the residue from ether affords needles of 3-(2-morpholino-hydroxyethyl)-5-phenylisoxazole (0.133 g, 22.2 %). mp. 133.5°–135.5°C.

Identification of this product with an authentic sample was carried out by mixed melting and by comparing the infrared absorption spectra.

EXAMPLE 15 (A connected operation, 1st step through 4th step)

To dimethylsulfoxide (23 g, 0.295 mole), there is added sodium amide (3.5 g, 0.09 mole) under nitrogen atmosphere to dissolve the latter while being heated at an oil bath temperature of 70°±5°C and stirred. The solution obtained is diluted with 10 ml of toluene and dripped into a solution of 3-methoxycarbonyl-5-phenylisoxazole (10 g, 0.049 mole) is 100 ml of toluene in about 4 minutes while being ice-cooled.

Simultaneously with the addition, an exothermic reaction takes place and a sodium salt precipitates to increase the viscosity of the solution which is subsequently stirred for about 30 minutes while being ice-cooled. The precipitated sodium salt (3-methylsulfinyl-sodioacetyl-5-phenylisoxazole or sodium 1-(5-phenylisoxazole-3-yl)-2-methylsulfinylethenoxide) is recovered by an aspiration with a No. 3 glass filter and washed with an additional 100 ml of toluene. The filtrate may be returned to a regeneration process for recovering toluene and dimethylsulfoxide.

The sodium salt thus obtained has a tautomeric structure of the formula:

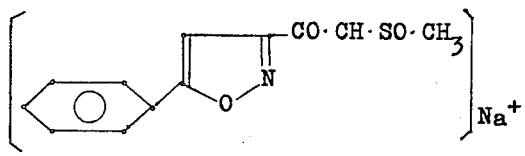

( Keto or Enol Form )

infrared absorption spectra of:
$\nu_{max}^{Nujol}$(cm$^{-1}$): 1615, 1595, 1575, 1530, 1440, 1355, 990, 975, 840, 750 and 580,
and a melting point ranging from 198°C to 202°C, but is suspended in the wet (with toluene) condition in 100 ml of toluene and thereto their is added dropwise 11.9 g (0.1 mole) of thionyl chloride in about 10 minutes while being stirred and ice-cooled to smoothly effect an exothermic reaction wherein sodium chloride precipitates in place of the sodium salt which disappears with the progress of the reaction.

After the addition of thionyl chloride and the subsequent stirring at the same temperature for 30 minutes, the insoluble substance in the solution, for instance, sodium chloride is removed by filtration with a No. 3 glass filter and washed with 100 ml of toluene.

The toluene layers are combined together and concentrated to dryness under reduced pressure by means of an aspirator at a bath temperature of 45°C to give a crude chloride (3-(2-methylthio-2-chloroacetyl)-5-phenylisoxazole) (16.4 g) as a crystalline residue.

This crude chloride, without further purification, is combined with 50 ml of toluene and the mixture is heated to 45°C to dissolve the chloride completely. To this solution of at the above temperature, there is added 9.5 g (0.11 mole) of piperidine all at once while being stirred.

The incorporation of the piperidine causes a precipitation of piperidine hydrochloride salt to make the solution viscous but the stirring still continues for an additional 40 minutes.

The hydrochloride salt is then removed from the solution by aspiration with a No. 3 glass filter and is washed with 100 ml of toluene.

The toluene layers (filtrate and washings) are then combined together and concentrated to dryness under reduced pressure at a bath temperature of 45°C to give crude 3-(2-methylthio-2-piperidinoacetyl)-5-phenylisoxazole (22.7 g) as a crystalline residue which is subsequently suspended in 100 ml of methanol without further purification.

To this suspension, there is added portionwise 1.4 g (0.037 mole) of sodium borohydride in about 10 minutes to effect an exothermic (+37°C) reaction with an evolution of gaseous mercaptan, a dissolution of the crystals and an accompanying precipitation of an insoluble substance.

After 20 minutes, the insoluble substance (0.4 g) is removed by aspiration with a No. 3 glass filter to recover a filtrate which is then concentrated to dryness at a bath temperature of 45°C to give a residue.

This residue is extracted twice with 100 ml of benzene each time and washed four times with 100 ml of water each time.

The extracts are combined together, dried over sodium sulfate and concentrated to dryness under reduced pressure to give crude 3-(2-piperidinyl-1-hydroxyethyl)-5-phenylisoxazole (12.1 g) as a crystalline residue which is then dissolved in 20 ml of methanol with heating (to 45°C) and allowed to stand in a refrigerator overnight with an addition of seed crystals.

The precipitated crystals are collected by aspiration with a No. 3 glass filter, washed with 15 ml of cooled (−10°C) methanol and dried in vacuo at room temperature for 6 hours to yield the intended product (5.15 g) as the first crop. mp. 104°–105.5°C.

The recovered and collected filtrate and washing are concentrated to dryness under reduced pressure by means of an aspirator at a bath temperature of about 45°C to give a residue which is then dissolved in 50 ml of benzene.

The benzene solution is shaken once with 50 ml of 4N hydrochloric acid and twice with each 50 ml of 1N hydrochloric acid each time to extract the basic portion thereof. The respective hydrochloric acid layers are each washed with 50 ml of benzene and combined together.

Neutralization of the combined hydrochloric acid layer with 45 ml of aqueous ammonia (28 %) under ice-cooling to make the solution basic (pH = 10) leads to a precipitation of the intended product as crystals.

The crystals are recovered by aspiration with a No. 3 glass filter, with 100 ml of water and dried over phosphoric oxide at room temperature in vacuo for 6 hours to yield the second crop (1.53 g). mp. 96°–99°C.

Total crop of the 3-(2-piperidinyl-1-hydroxyethyl)-5-phenylisoxazole is 6.68 g which amounts to an overall yield of 49.9 % calculated on the basis of the starting material, 3-methoxycarbonyl-5-phenylisoxazole.

What is claimed is:
1. A phenylisoxazole of the formula:

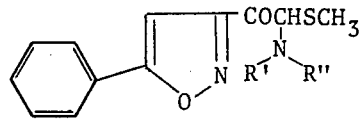

wherein R' and R'' each represent a lower alkyl group of 1 to 3 carbon atoms or R$^1$ and R$^{11}$ may be combined with the nitrogen atom to which they are attached to form a pyrrolidino or piperidino group.

2. 3-(2-Methylthio-2-piperidinoacetyl)-5-phenylisoxazole.
3. 3-(2-Methylthio-2-dimethylaminoacetyl)-5-phenylisoxazole.
4. 3-(2-Methylthio-2-diethylaminoacetyl)-5-phenylisoxazole.
5. 3-(2-Methylthio-2-dipropylaminoacetyl)-5-phenylisoxazole.
6. 3-(2-Methylthio-2-methylethylaminoacetyl)-5-phenylisoxazole.
7. 3-(2-Methylthio-2-methylisopropylaminoacetyl)-5-phenylisoxazole.
8. 3-(2-Methylthio-2-pyrrolidinoacetyl)-5-phenylisoxazole.

* * * * *